United States Patent [19]

Berman et al.

[11] 4,133,315

[45] Jan. 9, 1979

[54] METHOD AND APPARATUS FOR REDUCING OBESITY

[76] Inventors: Edward J. Berman; George A. Rowe, both of 3426 N. Meridian, Indianapolis, Ind. 46208

[21] Appl. No.: 754,568

[22] Filed: Dec. 27, 1976

[51] Int. Cl.² .............................................. A61B 17/00
[52] U.S. Cl. ................................ 128/303 R; 128/246; 128/344
[58] Field of Search ............................ 128/303 R, 344

[56] References Cited

U.S. PATENT DOCUMENTS

| 157,343 | 12/1874 | Molesworth | 128/344 |
| 3,046,988 | 7/1962 | Moreau et al. | 128/344 X |
| 3,081,773 | 3/1963 | Isaac | 128/303 R |

*Primary Examiner*—Dalton L. Truluck
*Assistant Examiner*—Milford Juten
*Attorney, Agent, or Firm*—Woodard, Weikart, Emhardt & Naughton

[57] ABSTRACT

An apparatus for reducing obesity in human beings having an inflatable bag to which a flexible tube is attached. The bag is positioned in the stomach, usually by swallowing, and the tube extends up through the esophagus and out of a nasal cavity or out from the abdomen when a gastrostomy is performed. The bag is inflated by attachment of a supply of fluid to the end of the tube, and then the tube is closed so that the bag will maintain its inflated conditon. With a portion of the open cavity of the patient's stomach occupied by the inflated bag, the patient will sense a feeling of being "filled-up" with only a small amount of food intake.

12 Claims, 9 Drawing Figures

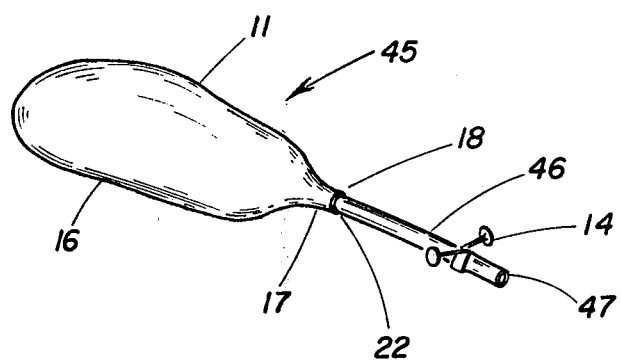
Fig. 7
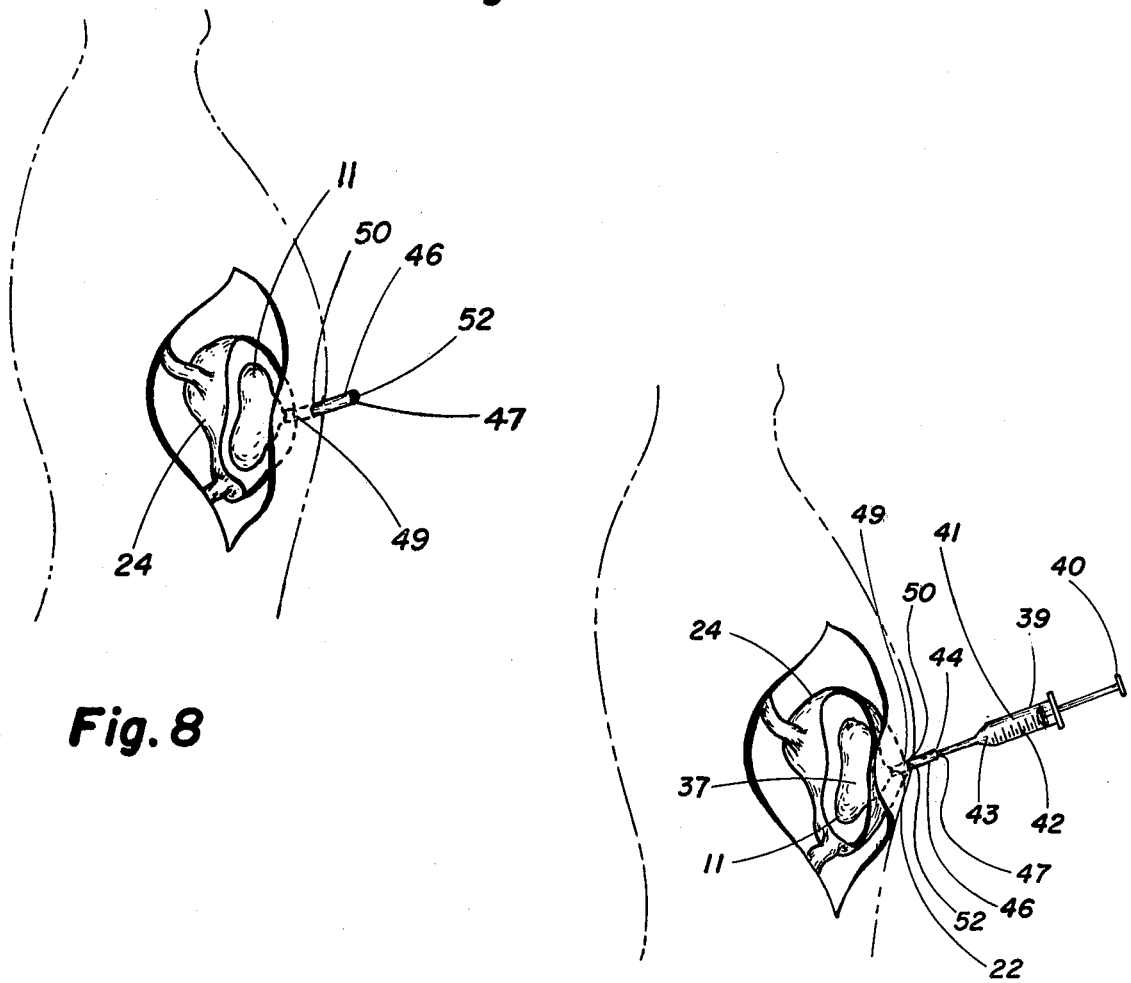
Fig. 8
Fig. 9

METHOD AND APPARATUS FOR REDUCING OBESITY

BACKGROUND OF THE INVENTION

1. Field of the Invention

This invention relates in general to dietary devices for medical treatment of obesity.

2. Description of the Prior Art

Those who have a problem with obesity have few options available to them with respect to a solution. The typical approach is to rely on the person's willpower to stick to a particular diet or to use diet pills to try and reduce the desire for food. These may be effective measures, depending upon the individual, but if the person is either physically or mentally unable to control his weight gain, he may be subject to more drastic measures, such as surgical reduction of the size of the stomach or bypassing much of the small intestines. Unfortunately, such measures have resulted in death to the patient in a substantial number of cases. Even if death is not the result, the operation is often permanent and the patient is still subjected to the after-effects once the problem with obesity is corrected. One approach to correcting obesity involves reducing the desire for food. This can be accomplished by partially filling the stomach so as to produce the sensation of being "filled-up." One way of accomplishing this is to place an inflatable, elastomeric bag in the stomach and inflate the bag with fluid.

Inflatable bag and tube combination devices are known in the field of medicine and have experienced use by the medical profession in the treatment of gastric disorders such as stomach ulcers and hemorrhages in the upper gastrointestinal tract. Cook, U.S. Pat. No. 3,227,154 discloses a device in which the bag must be fully inflated so that its impressionable-settable outer surface can make impressions in the walls of cavities which have restricted outlets. Another use of inflatable bag and tube combination devices as disclosed by Gawura, U.S. Pat. No. 3,768,484 and Seaman, U.S. Pat. No. 3,174,481, is to transfer and retain a cooling solution at a particular internal location. The bag acts merely as a container for this solution and the characteristic of being inflatable allows a single bag to be used with a wide range of cavity sizes. These prior art references all disclose tubes with a plurality of passageways and a liquid to inflate the bag.

In all of these situations, the use of the inflatable bag is of a short duration; once the diagnosis or treatment has been performed, the bag is removed from the human being's body. These types of applications do not require, nor do they benefit, from the bag remaining within the human being.

SUMMARY OF THE INVENTION

One embodiment of the method of reducing obesity in a person by decreasing the desire for food comprises the following steps. First, an inflatable bag is placed in a person's stomach. Next, the bag is caused to be inflated to a sufficient size to cause a suppression of the person's appetite. Finally, the bag is allowed to remain in the stomach while the person is eating.

Another embodiment of the present invention is an apparatus for reducing obesity in human beings comprising an inflatable, elastomeric bag and tube combination. The bag is sized for positioning in the human being's stomach and has a single opening to which a first tube is attached. It is an object of the present invention to provide an improved method of reducing obesity.

Related objects and advantages of the present invention will be apparent from the following description.

BRIEF DESCRIPTION OF THE DRAWINGS

FIG. 7 is a side elevation of another dietary apparatus forming an alternative embodiment of the invention.

FIG. 8 is an elevation showing the relative position of the FIG. 7 apparatus after a gastrostomy has been performed.

FIG. 9 is an elevation showing the positioned apparatus of FIG. 8 to which a supply source of fluid has been added.

DESCRIPTION OF THE PREFERRED EMBODIMENTS

Figure 1:
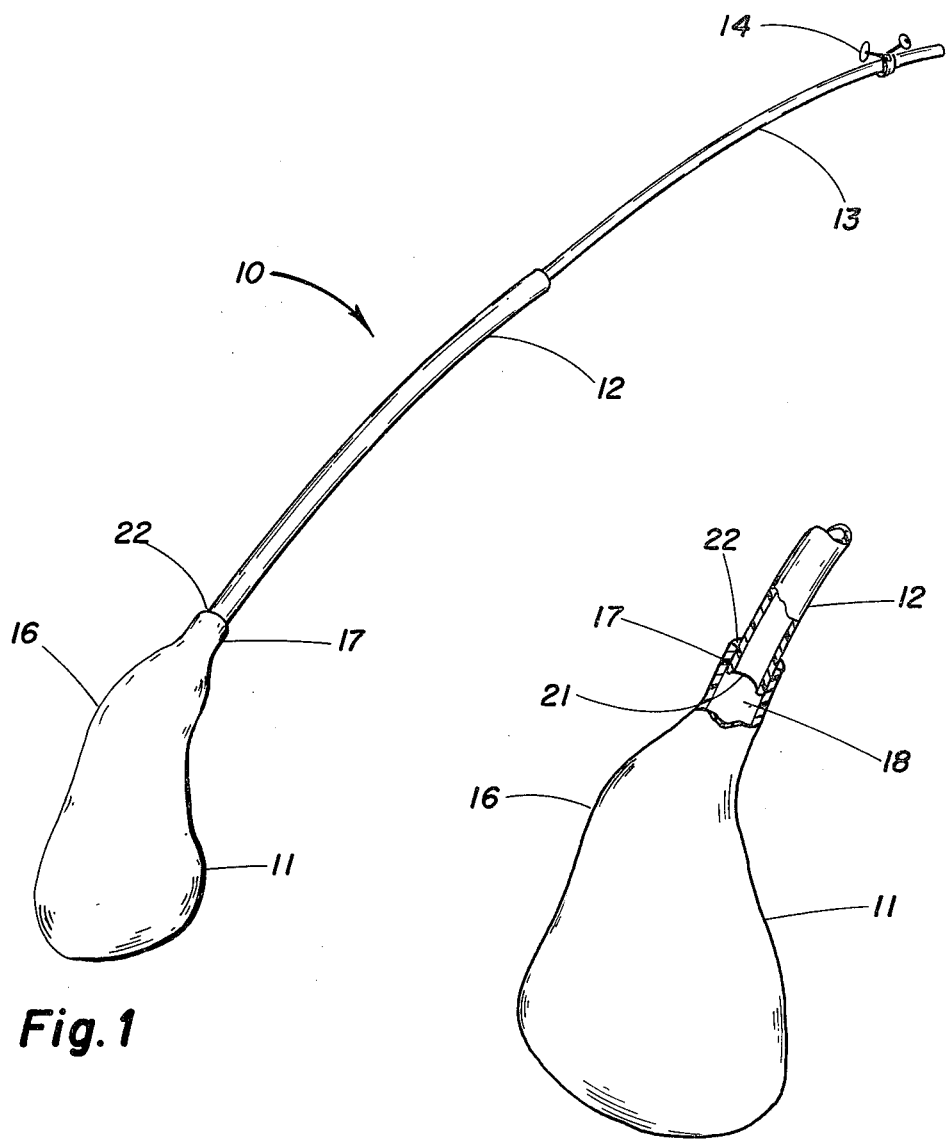
FIG. 1 is an elevation of the dietary apparatus of the invention showing the component parts.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
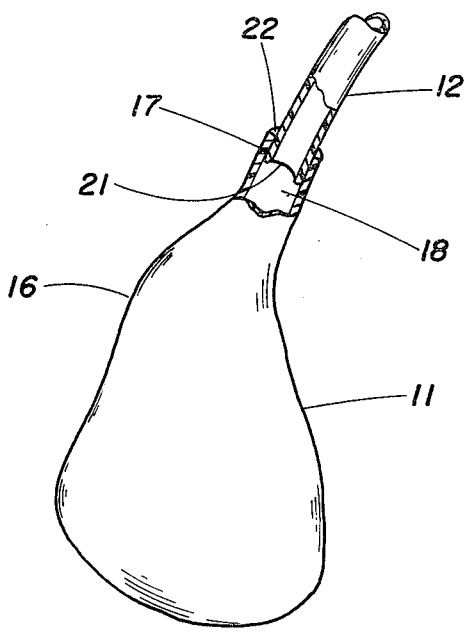
FIG. 2 is an enlarged fragmentary detail view of a tube bag attachment forming a part of FIG. 1.

Referring to FIG. 1, there is illustrated dietary apparatus 10 which includes an inflatable, elastomeric bag 11, a flexible tube 12, a flexible tube 13 and clamping means 14. Bag 11 has body 16 and neck portion 17 with the sole opening 18 (FIG. 2) of bag 11 being through neck portion 17. FIG. 2 is an enlarged fragmentary detail of apparatus 10 showing one end 21 of tube 12 inserted into the opening 18 and forming a sealed connection at point of attachment 22. Bag 11 and tube 12 may be joined by any suitable method such as by using an adhesive. Clamping means 14 is sized and constructed to be capable of closing the end of second tube 13 thereby forming a gas-tight seal. Preferably clamping means 14 should be manually operable with one hand such as a spring clip type of clamp. Tube 12 and 13 are also capable of being joined together in a gas-tight connection. Bag 11 and tubes 12 and 13 are constructed from substantially, physiologically inert and nontoxic material so as not to irritate the human body.

Figure 3:
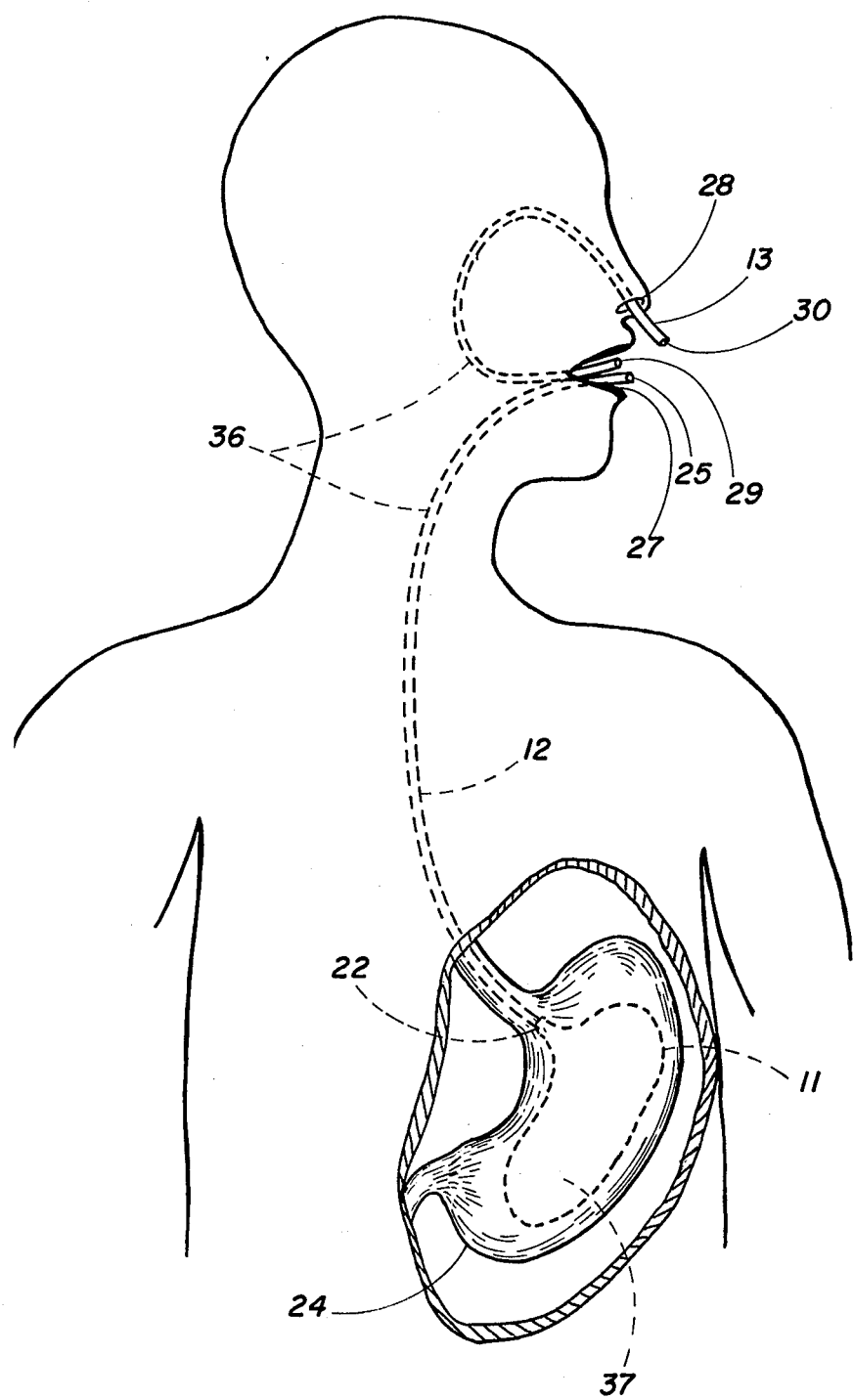
FIG. 3 is a fragmentary representation of the apparatus of FIG. 1 shown as positioned within a human being.

The method for reducing obesity involves placing bag 11, with tube 12 attached thereto, into the stomach of the person. This is normally done by having the person swallow the bag and tube. Tube 12 is of sufficient length to extend from the point of attachment 22 to bag 11 up through the person's esophagus and into the mouth cavity. FIG. 3 shows the resultant position of bag 11, tube 12, and the end 25 of tube 12 with respect to the person's stomach 24 and mouth cavity 27. The end 25 of tube 12 is not connected to tube 13 during the placement of bag 11 in stomach 24.

Figure 4:
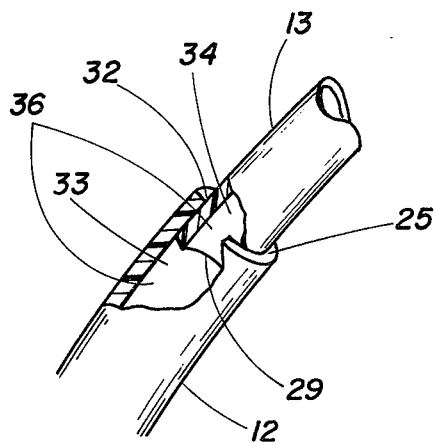
FIG. 4 is a fragmentary detail of the connection between two tubes of the FIG. 1 apparatus.

The next step of the method involves inserting tube 13 through one side of the person's nasal cavity, up through the nasal passage, and into the mouth cavity 27. The end 29 of tube 13 extends into the mouth cavity 27 while the second end 30 of tube 13 extends slightly out from the external opening 28 of the human being's nasal cavity. With tubes 12 and 13 in this position, FIG. 4 shows one possibility for joining of the end 25 of tube 12 to the end 29 of tube 13. This joining is performed outside the human being's mouth cavity 27 thereby making sealed connection 32. After the connection is made, the two tubes are positioned as shown and are of different diameters. This serves two purposes. First, the larger diameter tube which extends from the stomach (tube 12) may not be suitably sized to pass through the nasal cavity and passageway. Secondly, the insertion of tube 13 into tube 12 making connection 32 can be sealed by a press-fit or adhesive or similar suitable means, depending upon the size and material of the tubes. The size of the connection 32 should be kept to a minimum. If auxiliary clamps had to be used there would be increased discomfort to the person. Tube 12 has a sole passageway 33 extending longitudinally from first end 21 to second end 25. Likewise, tube 13 has a sole passageway 34 extending longitudinally from first end 29 to second end 30. The relationship between passageways 33 and 34 is shown by FIG. 4. Once tubes 12 and 13 are connected, a longer passageway 36 is created which extends from end 30 to the interior 37 of bag 11 and passes through sealed connection 32 (see FIGS. 3 and 4).

Figure 5:
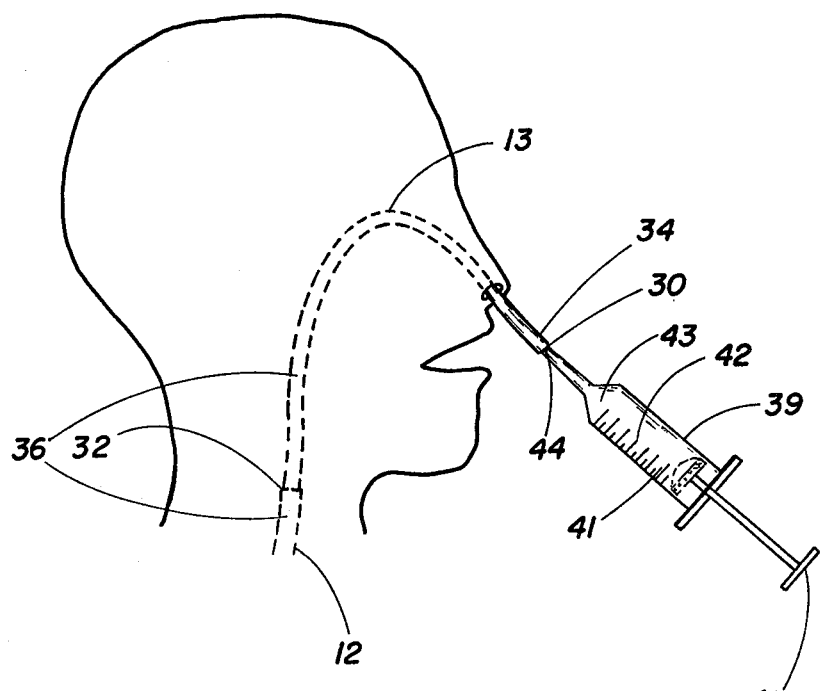
FIG. 5 is a representation of a tube of the FIG. 1 apparatus to which a supply source of fluid is shown as attached to one end of the tube.

FIG. 5 shows the final position of tubes 12, 13 and connection 32. A certain amount of slack in tubes 12 and 13 will be required to manipulate the ends 25 and 29 for the connection 32. Once the tubes are connected, end 30 can be pulled further out from opening 28 thereby taking up any slack in the mouth cavity 27 and drawing connection 32 of tubes 12 and 13 toward the rear of the human being's mouth. This is the position that the tubes 12, 13 of apparatus 10 will maintain for the length of time that apparatus is in the human being. Once in this position, the next step of the method is performed. A supply 39 of a distending agent which may be gas, water or other liquid, is attached to end 30 of tube 13. Although this supply 39 may comprise several forms, a hypodermic syringe is shown as possibly the preferred device for delivering the agent in a volume-controlled manner. Such a supply 39 of agent can have its plunger 40 drawn back to a predetermined point on chamber 41 as indicated by graduations 42. The graduations 42 indicate the volume of agent within chamber 41. With agent in supply 39, the tip 44 of supply 39 is inserted into passageway 34, with end 30 of tube 13 sealing around tip 44. Plunger 40 is then depressed forcing the agent in chamber 41 to pass through passageway 36 to the interior 37 of bag 11 (see FIG. 3), thereby inflating bag 11.

Figure 6:
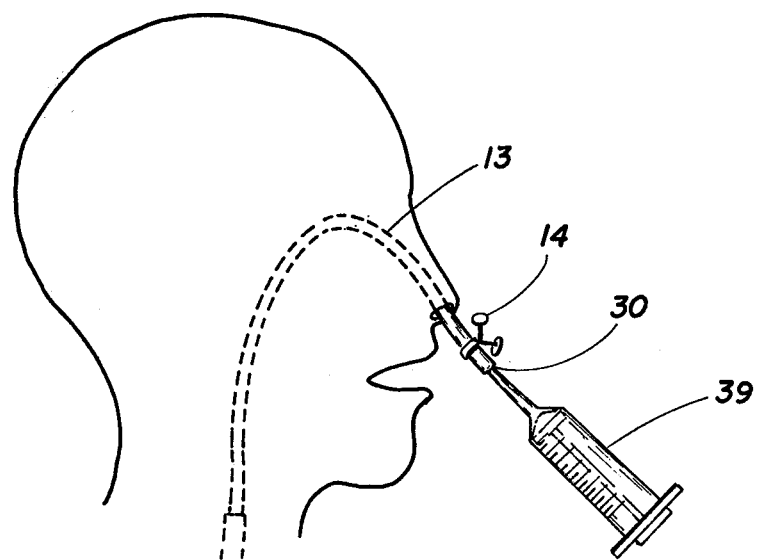
FIG. 6 shows the FIG. 5 apparatus with clamping means added.

Plunger 40 is stopped by tapered seat 43 at which time the chamber 41 is emptied and bag 11 is inflated. Prior to removal of supply 39, clamping means 14, as shown in FIG. 6, is attached to end 30 to close off tube 13 thereby preventing the agent which was emptied into bag 11 from escaping. Clamping means 14 may have to be placed over tube 13 in an open condition prior to attaching supply 39 if the design of clamping means 14 is such as to not permit attachment after supply 39 is inserted into passageway 34. It is possible to simply tie end 30 closed with a string or cord, but such a procedure presents disadvantages when the clamping means 14 is released for partial or complete deflation of bag 11.

In FIG. 7, there is illustrated apparatus 45 comprising an inflatable, elastomeric bag 11, flexible tube 46 and clamping means 14. Bag 11 having body 16, neck portion 17 and sole opening 18, is the same in all respects to bag 11 of FIGS. 1 and 2. Tube 46 is similar in material and structure to tube 12 except that tube 46 is of from three to nine inches in length from point of attachment 22 to end 47. Point of attachment 22 and the method of joining tube 46 to bag 11 follows the description given for tube 12 and bag 11 of FIGS. 1 and 2. The use of apparatus 45 involves placing bag 11, with tube 46 attached thereto, into the stomach 24 of the person by means of a gastrostomy (see FIG. 8). This operation involves making an opening 49 in the stomach wall, as well as an opening 50 in the abdomen adjacent to the opening 49 in the stomach and positioning the bag 11 in the stomach with the end 47 of tube 46 extending out through opening 49 and out through opening 50. With end 47 of tube 46 exited to the atmosphere from the person's body, a passageway 52 is provided from the end 47 of tube 46, longitudinally through tube 46 to the interior 37 of bag 11 (see FIG. 9).

The openings 49 and 50 may be sealed around the tube 46 in several ways. Natural sealing may be produced by inflating the bag and drawing the bag against the stomach so as to urge it against the peritoneum. This is accomplished by a pulling on the tube 46 and placing some sort of clamping means on the tube so as to hold the bag against the stomach wall and the stomach wall against the peritoneum. Auxiliary sealing means can also be provided for sealing the openings 49 and 50 such as a cuff or collar mounted on the tube 46 adjacent the bag 11. With the tube 46 extending from the abdomen of the human being, the next step involves attaching a supply 39 of agent to the end 47 of tube 46. The procedure of delivering agent to the interior of bag 11 thereby inflating bag 11 and the clamping closed of tube 46 is identical to the procedure described for FIGS. 5 and 6.

Either of the two methods which have been described will work equally well. The first method involving the two tubes and passage through the nasal cavity is more suitable for a shorter term use, while the gastrostomy method would involve a long-term use. A third procedure contemplated by the present invention is the combined usage of both methods. It is envisioned that the nasal passage positioning method would not be as convenient for prolonged periods of use as would the gastrostomy method. However, the nasal method requires no modification of the human anatomy. Therefore, it is possible to use the nasal passage method for a few weeks as a temporary measure, during which time the physician monitors the human being's weight gains and losses as a function of the timing and amount of bag distention. If the person responds favorably to the procedure and requires prolonged treatment, then the gastrostomy is performed. The stomach and abdominal placement by means of the gastrostomy allows the subject a more permanent way, as well as a more convenient way, to control his own degree of inflation of the bag without the need for close monitoring by the doctor. In the future, if the person's obesity problem is corrected and bag inflation within the stomach is no longer needed, the gastrostomy operation can be reversed by removing the device and, if necessary, surgically closing the openings in the stomach and abdomen.

With any of the methods described, the procedure of inflating the bag can be performed either as the human being eats or immediately before he starts to eat so that the desire for food is reduced. The inflated bag 11 reduces the open volume of the stomach cavity so that the human being experiences the sensation of fullness with only a small amount of food intake. The amount of intake can be controlled by the degree of inflation of the bag which is determined by the volume of agent drawn into and emptied from the chamber 41 of supply 39 of agent. In certain cases, the bag 11 can be inflated to such an extent that the patient would have virtually no desire for any food and actually skip a meal. It is envisioned that for human beings with an obesity problem the volume of the inflated bag will be of from one to two liters.

Once the human being has eaten, the bag can be deflated all at once, or it can be deflated gradually over a period of a few hours so as to simulate the condition of digestion occurring and the gradual reduction of stomach contents.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

When the term fluid is used in the claims which follow, it is intended to include both gases and liquids.

What is claimed is:

1. A method of reducing obesity in human beings which comprises:
    placing an inflatable bag in a human being's stomach;
    after said placing, causing the inflatable bag to be inflated to a sufficient size to cause a suppression of appetite;
    allowing the inflatable bag to remain in the stomach while the human being is eating; and
    alternately inflating and deflating the bag and having the human being eat orally by placing food in the mouth and swallowing.

2. The method of reducing obesity of claim 1 in which a tube is attached to said inflatable bag thereby allowing the level of inflation of the bag to be changed.

3. The method of reducing obesity of claim 2 in which said tube extends up the human being's esophagus and out the human being's nasal cavity.

4. The method of reducing obesity of claim 2 in which said tube extends through an opening in the human being's stomach wall and out an opening in the human being's abdomen.

5. The method of reducing obesity of claim 1 in which said step of causing the inflatable bag to be inflated is performed by inflating to a size of from one to two liters.

6. The method of reducing obesity of claim 1 in which said step of allowing the inflatable bag to remain is performed by allowing the bag to remain in the stomach for at least three days.

7. A method or reducing obesity in human beings by decreasing the desire for food which comprises:
    placing an inflatable, elastomeric bag having a first, flexible tube attached thereto, into the stomach of the human being through the mouth cavity of the human being so that one end of the tube extends into the mouth cavity of the human being;
    inserting a second, flexible tube through the opening in one side of the human being's nasal cavity in such a manner that one end is projected into the mouth cavity, and the other end of the second tube extends from the nose;
    connecting the one end of the first tube to the one end of the second tube so that a passageway is provided through the tubes from the other end of the second tube, outside the nasal cavity, to the interior of the bag;
    delivering an amount of a fluid through the other end of the second tube, from a supply, through said passageway for inflation of the bag; and
    sealing off the other end of the second tube so that the bag maintains its inflated condition.

8. A method of reducing obesity in human beings as recited in claim 7, wherein the delivery of an amount of fluid is performed in a volume-controlled manner by attaching a graduated syringe containing said fluid to the other end of the second tube and depressing the plunger of the syringe.

9. A method of reducing obesity in human beings as recited in claim 7 further comprising:
    opening of the other end of the second tube once the bag has maintained its inflated condition for a period of time so that the bag will deflate;
    repeating the inflating and deflating cycle several times over a period of a few weeks while monitoring the human being's weight gains and losses;
    removing the bag and first and second tubes from the human being;
    performing a gastrostomy on the human being whereby an opening is made in the stomach wall and an adjacent opening is made in the human being's abdomen for the purpose of placing a further inflatable elastomeric bag having a further flexible tube attached thereto into the stomach of the human being;
    drawing out through both openings to a point of exit to the atmosphere on the human being's abdomen one end of the further tube so that a passageway is provided through the tube to the interior of the bag;
    delivering an amount of fluid through the one end of the further tube, from a supply, through said passageway for inflation of the bag; and
    sealing off the one end of the further tube so that the bag maintains its inflated condition.

10. A method of reducing obesity in human beings by decreasing the desire for food which comprises:
    placing an inflatable, elastomeric bag having a first, flexible tube attached thereto, into the stomach of the human being through the mouth cavity of the human being;
    performing a gastrostomy on the human being whereby an opening is made in the stomach wall and an adjacent opening is made in the human being's abdomen;
    drawing out through both openings to a point of exit to the atmosphere on the human being's abdomen one end of the tube so that a passageway is provided through the tube to the interior of the bag;
    delivering an amount of fluid through the one end of the tube, from a supply, through said passageway for inflation of the bag; and sealing off the one end of the tube so that the bag maintains its inflated condition, and alternately inflating and deflating the bag and having the human being eat orally by placing food in the mouth and swallowing.

11. A method of reducing obesity in human beings as recited in claim 10, wherein the delivery of an amount of fluid is performed in a volume-controlled manner by attaching a graduated syringe containing said fluid to the one end of the tube and depressing the plunger of the syringe.

12. An apparatus for reducing obesity in human beings by decreasing the desire for food which comprises:

an inflatable, elastomeric bag sized for positioning in the human being's stomach, the bag of a substantially physiologically inert and nontoxic material, said bag having an inflatable body portion, a neck portion and only one bag opening, said one bag opening being in said neck portion;

a first flexible tube having only one passageway, said tube having a first end connected to the opening in said neck portion of said bag and also having a second end, said tube being of a sufficient length between said first and second ends to extend from the neck portion of said bag up through a human being's esophagus into the cavity of the human being's mouth;

a second flexible tube of smaller diameter than said first tube having only one passageway and of a sufficient length to extend from the opening of one of the human being's nasal cavities to the cavity of the human being's mouth, said tube having a first end and a second end, said first end being adapted to exit at said cavity of the mouth, said second end being adapted to extend from said opening of the nasal cavity both tubes being of a substantially, physiologically inert and nontoxic material;

means for joining the second end of the first tube to the first end of the second tube in a sealed connection, thereby forming a passageway through the tubes from said opening of the nasal cavity to the interior of the bag;

means for closing said second end of the second tube to prevent fluid within said bag from escaping to the atmosphere whereby upon opening of said means the fluid is allowed to escape to the atmosphere thereby deflating the bag.

* * * * *

UNITED STATES PATENT AND TRADEMARK OFFICE
CERTIFICATE OF CORRECTION

PATENT NO. : 4,133,315
DATED : January 9, 1979
INVENTOR(S) : Edward J. Berman; George A. Rowe It is certified that error appears in the above-identified patent and that said Letters Patent are hereby corrected as shown below:

In column 7, line 15 after the word "bag" please insert the word --being--.

Signed and Sealed this

Twenty-fourth Day of April 1979

[SEAL]

Attest:

RUTH C. MASON
Attesting Officer

DONALD W. BANNER
Commissioner of Patents and Trademarks